United States Patent [19]

Chagnon et al.

[11] Patent Number: 5,071,076

[45] Date of Patent: Dec. 10, 1991

[54] METHOD FOR PRODUCING MAGNETIC MICROPARTICLES FROM METALLOCENES

[75] Inventors: Mark S. Chagnon, Pelham, N.H.; Tracy Hamilton, Lowell; John R. Ferris, Newburyport, both of Mass.

[73] Assignee: Omni Quest Corporation, Atkinston, N.H.

[21] Appl. No.: 565,801

[22] Filed: Aug. 10, 1990

[51] Int. Cl.$^5$ .............................................. B02C 19/12
[52] U.S. Cl. ........................................ 241/21; 241/29
[58] Field of Search ............................ 241/21, 30, 29; 23/293 R

[56] References Cited

U.S. PATENT DOCUMENTS

| | | |
|---|---|---|
| 2,680,756 | 6/1954 | Pauson . |
| 2,791,597 | 5/1957 | Anzilotti et al. . |
| 3,620,584 | 11/1971 | Rosensweig . |
| 4,454,282 | 6/1984 | Bradshaw et al. . |
| 4,604,222 | 8/1986 | Borduz et al. . |
| 4,604,229 | 8/1986 | Raj et al. . |
| 4,672,040 | 6/1987 | Josephson . |
| 4,770,183 | 9/1988 | Groman et al. . |

OTHER PUBLICATIONS

Pykett et al., Nuclear Magnetic Resonance, pp. 157–167 (Apr. 1982), "Principles of Nuclear Magnetic Resonance Imaging".
M. Pourfarzaneh, The Ligand Quarterly, 5(i), pp. 41–47 (1982), "Product and Use of Magnetizable Particles in Immunoassay".
T. F. Budinger et al., Science (Oct. 1984), pp. 288–298, "Nuclear Magnetic Resonance Technology for Medical Studies".
I. L. Pykett, Scientific America 246, pp. 78–88 (May 1982), "NMR Imaging in Medicine".
Chemtech, Mar. 1982, Magnetic Separations in Chemistry and Biochemistry, pp. 172–179 by Bernard L. Hirschbein, Duncan W. Brown and George M. Whitesides.
Nature, vol. 268, Aug. 4, 1977, Application of Magnetic Microspheres in Labeling and Separation of Cells, pp. 437–438, by R. S. Molday, S. P. S. Yen, A. Rembaum.
Brintzinger et al., *J. of the American Chemical Society*, 92(21):6182–6185 (1970).
M. Rausch et al., *J. Chemical Education*, 346:268–272 (1957).
E. W. Rockett and G. Marr, *J. Organometallic Chem.*, 211:215–278 (1981).
D. E. Bublitz and K. L. Rinehart, Jr., *Organic Reactions*, 17:1–154 (1969).

*Primary Examiner*—Mark Rosenbaum
*Attorney, Agent, or Firm*—Hayes, Soloway, Hennessey & Hage

[57] ABSTRACT

A novel method for producing magnetic microparticles from metallocenes is disclosed. The method involves combining an aqueous slurry of the metallocene and an aqueous slurry of a metal hydroxide and milling the slurries together. Fine magnetic particles are produced using the present method.

29 Claims, No Drawings

METHOD FOR PRODUCING MAGNETIC MICROPARTICLES FROM METALLOCENES

BACKGROUND OF THE INVENTION

Magnetic microparticles have many applications in such diverse fields as clinical biology, chemistry, medicine, electronics and physics. For example, in the field of clinical biology, small magnetically responsive particles have been used in vitro separations, where the particle is coated and/or functionalized so that a reactive group, such as an affinity agent, can be attached to the particle. The particles are then dispersed in a sample, where reactive groups or affinity agents react specifically with a target molecule. The magnetic particle containing the target molecule is then recovered by applying a magnetic field to the sample, thereby separating the magnetic particles from the sample. The target molecules can then be removed from the magnetic particles. Magnetic particles functionalized with chemically reactive groups can be used in chemical separations. Separation techniques using magnetic particles are well known in the art. Molday et al., *Nature*, 268:437-438 (1977); B.L. Hirschbein et al., *Chemtech*, March, 1982, pp. 172-179 (1982); M. Pourfarzaneh. *The Ligand Quarterly*, 5(1):41-47 (1982); Josephson, U.S. Pat. No. 4,672,040 (1987) and references cited therein.

Very small magnetic particles have important medical applications in the fields of in vivo imaging. In one application, the magnetically responsive particles are utilized as contrast agents for magnetic resonance imaging (MRI). MRI is used for a variety of clinical diagnostic purposes, including detection of cancerous lesions in reticuloendothelial tissues, detection of intenstinal lesions, or liver diseases, such as hepatitis and cirrhosis. Clinical usage of MRI for diagnostic purposes is described, for example, by Groman and Josephson in U.S. 4,770,183 (1988); Pykett et al., *Nuclear Magnetic Resonance*, pp. 157.167 (April, 1982) and T F. Budinger et al., *Science*, pp. 288.298 (October, 1984). Contrast agents are used in MRI to define selected tissues and to differentiate from surrounding tissue.

Magnetically responsive particles also have many applications in the fields of electronics and computers. For example, ferrofluids containing small magnetically responsive particles dispersed in a carrier fluid are used as seals in computer disk drives, when they act as spindle sealants and as electrical grounds to prevent an electrical charge from building up in the drive shaft. Small magnetic particles dispersed in various polymeric carriers have been used to coat magnetic tapes and to form magnetic stripes which can be used to store information The use of ferrofluids in magnetic recording media and as sealants in computer disk drives has been described in: Ootani et al. U.S. Pat. No. 4,786,551 (1988); Papalos U.S. Pat. No. 4,770,952 (1988); Yamaguchi et al., U.S. Pat. No. 4,420,532 (1983); Bradshaw et al. U.S. Pat. No. 4,454,282 (1984); Koike et al., U.S. Pat. No. 4,407,721 (1983); Borduz and Raj, U.S. Pat. No. 4,604,229 (1986) and U.S. Pat. No. 4,604,222 (1986); Rosenswerg, U.S Pat. No. 3,620,584 (1971); and Chagnon, U.S. Pat. No. 4,356,092 (1982).

Small magnetic particles can exhibit different types of magnetic behavior based on their crystal size. The particles may be ferromagnetic, paramagnetic or superparamagnetic. Ferromagnetism occurs in particles in which the unpaired electrons in the magnetic materials interact, that is, they are highly coupled. Ferromagnetic materials are characterized by high magnetic susceptibilities in the presence of an applied magnetic field, and they retain their magnetic properties after the externally applied magnetic field has been removed. Magnetic susceptibility is the degree of response to an applied magnetic field. Ferromagnetism results only when the unpaired electrons are contained in a crystalline lattice or metallic complex and is not a property of individual molecule-like ions in solutions or gases. Ferromagnetic materials include metallic iron and certain metal oxides such as gamma ferric oxide (gamma-$Fe_2O_3$) or magnetic particles which are larger then about 0.1 micron in diameter.

Paramagnetism occurs in particles that contain unpaired electrons which do not interact, and are not coupled, such as ions in solutions or gases with unpaired electrons. Paramagnetic materials are characterized by a weak magnetic susceptibility. Paramagnetic particles become weakly magnetic in the presence of a magnetic field, and rapidly demagnetize once the external field is removed.

Superparamagnetic particles possess characteristics of both paramagnetic and ferromagnetic materials. Like paramagnetic particles, superparamagnetic particles rapidly demagnetize after the external magnetic field is removed; and like ferromagnetic particles, possess high magnetic susceptibility. Iron oxides such as magnetite or gamma ferric oxide exhibit superparamagnetic behavior when the crystal diameter falls significantly below that of ferromagnetic materials For cubic magnetite and gamma ferric oxide, this crystal diameter is about 300 angstroms (.03 microns) J. Dunlop, *J. Geophys. Rev.*, 78:1780 (1972; Bate *In: Ferromagnetic Materials*, Vol. 2 Wohlfarth (ed.), p. 439 (1980). Since iron oxide crystals are generally not of a single uniform size, the average size of purely ferromagnetic iron oxides is substantially larger that 300 angstroms. For example, ferromagnetic iron oxide used in magnetic recording materials consists of needle-like particles which are about 0.35 microns long and 0.06 microns thick. Ferromagnetic particles for data recording are generally between 0.1 and 10 microns in length. Jorgenson, *The Complete Handbook of Magnetic Recording*, p.35 (1980). For a given type of metal or metal oxide crystal, purely ferromagnetic crystals have average dimensions many times larger that purely superparamagnetic crystals of the same material.

Magnetic particles exhibiting specific forms of magnetic behavior are appropriate for applications in the various diverse fields in which such particles are used. For example, for use in MRI, superparamagnetic particles are preferred because superparamagnetism profoundly alters nuclear magnetic reasonance (NMR) images. Ferromagnetic particles are preferred for use in most electronic, magnetic recording and computer applications. Thus, a method for making magnetic particles having desired properties would be useful for many applications.

SUMMARY OF THE INVENTION

The present invention provides a process for producing magnetic particles from metallocenes. In the present process, an aqueous slurry of the metallocene is combined with an aqueous slurry of a metal hydroxide in a high energy mill, such as ball mill or sand mill, and the combined slurries are milled together for a period of time sufficient to form magnetic particles.

It has been discovered that premilling of the metallocene and metal hydroxide in separate vessels for varying periods of time alters the particle size of the resulting magnetic particles. Longer milling times generally result in smaller particles. The magnetic character of the particles is a function of their size. Thus, the process allows magnetic particles having desired properties to be produced.

The present method has several advantages over conventional precipitation processes: The present invention method allows the particle size of the magnetic particles to be controlled, which is not easily accomplished with precipitation methods. Smaller particle sizes can be obtained, particle size distributions can be tailored to a desired level based on Premilling times of each reactant and milling times of the mixtures and mixed oxide lattices can be prepared according to the present method using various metallocenes.

DETAILED DESCRIPTION OF THE INVENTION

The present process provides method for making magnetic particles from metallocenes.

Metallocenes are cycopentodienyl coordinate complexes of metals. The cyclopentadienyl group, $C_5H_5$, has long been known to form complexes with metals or metalloidal atoms. Metallocenes which are useful in the present process are cyclopentadienyl complexes of transition metals. The transition-metals include, for example iron (Fe), magnesium (Mg), manganese (Mn), cobalt (Co), nickel (Ni), zinc (Zn) and copper (Cu). Particularly useful metallocenes are ferrocene $(C_5H_5)_2Fe$, nickelocene, $(C_5H_5)_2Ni$, and cobaltocene, $(C_5H_5)_2Co$. Metallocenes have the general formula $(C_5H_5)_2M$, wherein M is the metal and have a "sandwich" configuration. Ferrocene, for example, has the following sandwich structure:

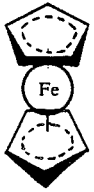

The structure of metallocenes endows these molecules with high thermal stability (e.g., up to about 500° C. for ferrocene). The characteristics and preparation of metallocenes is discussed in *Advantages In Organic Chemistry*, 3rd ed., F.A. Cotton and G. Wilkinson, John Wiley & Sons, Inc., pp. 736-743 (1972) and in *Chemistry of the Iron Group Metallocenes*, by M. Rosenbaum, John Wiley & Sons, Inc., (1965).

In the present process, an aqueous slurry of the metallocene is provided. The slurry can be prepared, for example, by combining the metallocene compound and water, and mixing or by milling in a high energy mill, such as a sand mill or a ball mill. The length of time for which the slurries are milled will depend upon the particle size of the product which is desired The slurry will generally contain from about 0.1 to about 40 percent (%) by weight of the metallocene. A slurry containing from about 20 to about 25% by weight metallocene is particularly useful.

The aqueous metallocene slurry is combined with a second aqueous slurry of a metal hydroxide. The choice of metal hydroxide will depend upon the properties of the particles which are desired. For example, to produce magnetite particles, iron (II) hydroxide (ferrous hydroxide) is used. Other metal hydroxide which can be used to produce magnetic particles, for example, include cobalt (II) hydroxide, cobalt (III) hydroxide. iron (III) hydroxide and nickel hydroxide. Slurries of these metal hydroxides can be prepared, for example, by precipitating a salt of the metal (e.g. chloride or sulfate salt) in an aqueous medium using a base, such as sodium hydroxide or ammonium hydroxide. An aqueous iron (II) hydroxide slurry can be prepared, for example, by precipitating an aqueous solution of ferrous chloride or ferrous sulfate with ammonium or sodium hydroxide to form ferrous hydroxide (FeO(OH)). The resulting gelatinous precipitate of iron (II) hydroxide is filtered, and the solid material is collected, combined with water and milled in a high energy mill to form the slurry. The metal hydroxide slurry can contain, for example, from about 0.1 to about 40 percent (%) by weight of the metal hydroxide, preferably about 10-20% by weight.

The two slurries are combined and the mixture is milled, for example in a high energy mill, such as a commercial ball or sand mill, for a period of time sufficient to form fine magnetic particles, generally for about 1 hour to about 60 hours. Generally, the longer the milling step, the smaller the particles which are formed.

In a preferred embodiment of the present invention, magnetite particles are formed from iron (II) hydroxide and ferrocene according to the following equation:

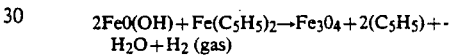

In this process, the iron (II) hydroxide powder is milled in intimate contact with the ferrocene. Over a period of about 20 to 40 hours the two materials react by slow dissociation of the hydroxide to form magnetite, free cyclopentene, water and hydrogen. It is necessary to allow sufficient void space in the mill, or to vent the mill periodically to accomodate the release of the hydrogen gas formed during the reaction.

The resulting magnetite particles have a magnetization of about 5500 gauss/domain calculated from the equation: $\phi = Ms/Md$ wherein:

$\phi = \%$ vol magnetite $M_s =$ saturation magnetization $M_d =$ domain magnetization.

It has further been discovered that pre-milling of the metallocene and metal hydroxide in separate vessels for various periods of time will alter the particle size of the resulting magnetic particles. Milling of the starting materials (e.g.. ferrocene and iron (II) hydroxide) for 5 hours prior to mixing, for example resulted in formation of 100 angstrom (A) particles. Pre-milling for 24 hours resulted in formation of 40 A particles. Table 1 sets out the properties of magnetite particles obtained by pre-milling a ferrocene slurry and an iron (II) hydroxide slurry for 5 hours, combining the two slurries and milling them together for various times

TABLE 1

Particle Size of Magnetite Crystals After
Pre-Milling Reactants for 5 Hours and Varying
Mill Times of the Mixture

| Time Hours | Particle Size (Angstroms) | Particle Size Distribution (% of Nominal) | Md (Gauss) |
|---|---|---|---|
| 1 | 1500 | 50 | 1000 |
| 2 | 1000 | 25 | 1900 |
| 5 | 150 | 20 | 3660 |

TABLE 1-continued

Particle Size of Magnetite Crystals After Pre-Milling Reactants for 5 Hours and Varying Mill Times of the Mixture

| Time Hours | Particle Size (Angstroms) | Particle Size Distribution (% of Nominal) | Md (Gauss) |
|---|---|---|---|
| 10 | 120 | 15 | 4880 |
| 20 | 50 | 5 | 5500 |
| 24 | 40 | 5 | 5500 |
| 48 | 30 | 5 | 5500 |
| 60 | 25 | 5 | 5500 |
| 100 | 15 | 5-8 | 5500 |

Table 2 shows the particle size of magnetite crystals obtained when the iron (II) hydroxide slurry is pre-milled for 5 hours and the ferrocene slurry is not pre-milled.

TABLE 2

Properties of Magnetite Crystals After Premilling FeO(OH) Slurry and Varying Mill Times of the Mixture

| Time Hours | Particle Size (Angstroms) | Particle Size Distribution (% of Nominal) | Md (Gauss) |
|---|---|---|---|
| 1 | 1500 | 10 | 1300 |
| 2 | 1500 | 5 | 1600 |
| 3 | 1000 | 5 | 1900 |
| 5 | 100 | 5 | 2100 |
| 10 | 50 | 2-3 | 2900 |
| 20 | 20 | 5 | 5500 |
| 24 | 15 | 5 | 5500 |
| 60 | 15 | — | 5600 |

Table 3 shows the particle size of magnetite crystals obtained when the reactants are not premilled.

TABLE 3

Properties of Magnetite Crystals with No Premilling of Reactants and Varying Mill Times of the Mixture

| Time Hours | Particle Size (Angstroms) | Particle Size Distribution (% of Nominal) | Md (Gauss) |
|---|---|---|---|
| 1 | Gel | — | — |
| 2 | Gel | — | — |
| 3 | Gel | — | — |
| 5 | 2000 | 50 | 1500 |
| 10 | 1800 | 20 | 2900 |
| 20 | 1500 | 10 | 5500 |
| 24 | 1400 | 5 | 5500 |
| 60 | 1000 | 5 | 5600 |
| 100 | 600 | 5 | 5500 |

Thus, the properties of the particles, e.g., the crystal size, distribution, and magnetization, can be controlled by varying the composition and pre-milling times of the initial slurries, and the milling times of the mixture.

If the reactants (i.e., the metallocene and metal hydroxide slurries) are premilled, for example, for a period of 5 hours, and the slurry mixture is milled in excess of 24 hours, particles having an average diameter of about 50 angstroms or less are produced. If the reactants are not premilled, and the mixture is milled for about 20 hours, particles having an average diameter of about 1500 angstroms are produced.

Particles of about 50 angstroms in diameter or less are useful for in vivo diagnostic applications, such as MRI imagery and for in vivo magnetic drug targeting. For this purpose, the particles can be coated and functionalized so that a bioaffinity agent can be attached to the particles. Methods for coating, functionalizing and using magnetic particles is described in co-pending U.S. patent application Ser. No. 07/566,169, by M.S. Chagnon, filed concurrently herewith, the teachings of which are hereby incorporated herein by reference.

Particles of about 100 angstroms in diameter are superparamagnetic and are highly responsive to externally applied magnetic fields. Such particles are useful starting materials for magnetic fluid colloids which can be applied as seals in computer disk drives, for example superparamagnetic particles are useful for in vitro separations.

Particles of 1000–10,000 angstroms in diameter are typically ferromagnetic particles which are useful for magnetic recording applications, for example, making magnetic tapes or floppy disks.

For each of the above applications, it is necessary to control the particle size and size distribution of the crystals in order to impart the appropriate magnetic field response, and dispersion rheology.

The invention will be illustrated by the following examples.

EXAMPLES

Example 1

Preparation of Magnetic Particles by Reaction of Particulate Ferrocene and Iron (II) hydroxide A 20% ferrocene (dicyclopentadenyliron, Strem Chemical Co., Newburyport, MA) slurry was prepared by combining 20 g of ferrocene with 80 g of water and adding to a commercial ball mill. The mill was filled halfway with $\frac{1}{4}''$ stainless steel balls and the slurry was milled for a period of 2 hours.

A second, ferrous hydroxide (iron (II) hydroxide) slurry was made according to the following procedure. An aqueous solution containing 20 g of ferrous sulfate (VWR Scientific) was precipitated using 50 g of ammonium hydroxide concentrate to form gelatinous ferrous hydroxide. The gel was filtered and the filtrate washed with 5 to 100 g volumes of water. The washed gel was then made into a 10% aqueous slurry and milled as previously described for 2 hours.

The ferrocene and hydroxide slurries were mixed, and the mixture was milled for one day to form fine $Fe_3O_4$ particles. The particles were about 100 Å in diameter and had a magnetic field response of about 4800 gauss.

Example 2

Preparation of Nickel-Ferrite Particles

Nickel ferrite particles were prepared according to the procedure set out in Example 1, except that a mixture of 50 g of a 20 % (by weight) nickelocene slurry (dicyclopentadenylnickel; Strem Chemical Co., Newburyport MA) and 50 g of the ferrocene slurry were used in lieu of the 100 g of ferrocene in Example 6. Magnetically responsive nickel-ferrite particles having a particle size of about 100 Å were produced by this method.

Example 3

Preparation of Cobalt-Ferrite Particles

Subdomain cobalt-ferrite particles were prepared according to the procedure set out in Example 1, except that a mixture of 50 g of a 20% (by weight) cobaltocene slurry (dicyclopentadenylcobalt; Strem Chemical Co., Newburyport, MA) and 50 g of the ferrocene slurry were used in lieu of the 100 g of the ferrocene slurry in Example 6. Magnetically responsive cobalt-ferrite particles having a particle size of about 100 A were produced by this method.

Example 4

Preparation of Ferromagnetic Particles

Ferromagnetic magnetite particles were prepared according to the procedure set out in Example 1, except that the ferrocene slurry and the ferrous hydroxide slurry were milled separately for 5 hours, and the slurry mixture was milled for about 10 hours. Magnetite particles having a crystal size of about 100 angstroms and a magnetic field response of 4880 gauss were obtained.

Example 5

Preparation of Very Small (Subdomain) Magnetite Particles

Very small particles having diameter of less than 50 angstroms were produced by prepared according to the procedure set out in Example 4, except that the slurry mixture was milled for about 24 hours. Magnetite crystals having a particle size of from about 40 angstroms, and a magnetic field response of 5500 gauss.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A process for producing magnetic particles comprising the steps of:
   a. combining an aqueous slurry of a metallocene with an aqueous slurry of a metal hydroxide; and
   b. milling the combination produced in step (a) to form a slurry of magnetic particles.

2. A process of claim 1 wherein the metallocene is selected from the group consisting of: ferrocene, cobaltocene, nickelocene and mixtures thereof.

3. A process of claim 1 wherein the aqueous metallocene slurry is prepared by milling metallocene and water.

4. A process of claim 1 wherein the metal hydroxide is selected from the group consisting of: iron (II) hydroxide, iron (III) hydroxide, cobalt (II) hydroxide, cobalt (III) hydroxide and nickel hydroxide.

5. A process of claim 4, wherein the aqueous metal hydroxide slurry is an iron (II) hydroxide slurry prepared by precipitating an aqueous solution of ferrous sulfate with ammonium hydroxide under conditions sufficient to form iron (II) hydroxide.

6. A process of claim 1 wherein the milling step is performed using a ball mill.

7. A process of claim 1 wherein the metallocene slurry contains about 0.1 to about 40% by weight metallocene.

8. A process of claim 7 wherein the metallocene slurry contains from about 20 to about 25% by weight metallocene.

9. A process of claim 1 wherein the metal hydroxide slurry contains about from about 0.1 to about 40% by weight of the metal hydroxide.

10. A process of claim 9 wherein the metal hydroxide slurry contains from about 10 to about 20% by weight of the metal hydroxide.

11. A process of claim 1 further comprising the step of premilling the metallocene slurry.

12. A process of claim 1 further comprising the step of premilling the metal hydroxide slurry.

13. A process of claim 1 further comprising premilling both the metallocene and metal hydroxide slurries.

14. A process of claim 1 wherein the milling step is performed using a sand mill.

15. A process of claim 1 wherein the combination is milled for about 1 to 100 hours.

16. A process of claim 1 wherein the combination is milled for about 20 to 40 hours.

17. A process for producing magnetite particles comprising the steps of:
   a. combining an aqueous slurry of ferrocene and an aqueous slurry of iron (II) hydroxide; and
   b. milling the combination produced in step (a) to form a slurry of magnetite particles.

18. A process of claim 17 wherein the ferrocene slurry contains from about 0.1 to about 40% by weight ferrocene.

19. A process of claim 18 wherein the ferrocene slurry contains from about 20 to about 25% by weight ferrocene.

20. A process of claim 17 wherein the iron (II) hydroxide slurry contains from about 0.1 to about 40% by weight iron (II) hydroxide.

21. A process of claim 20 wherein the iron (II) hydroxide slurry contains about 10% by weight iron (II) hydroxide.

22. A process of claim 17 further comprising the step of pre-milling the ferrocene slurry.

23. A process of claim 17 further comprising the step of pre-milling the iron (II) hydroxide slurry.

24. A process of claim 17 wherein the comprising the additional step of premilling both the ferrocene and iron (II) hydroxide slurries.

25. A process of claim 24 wherein the slurries are pre-milled for about 5 hours.

26. A process of claim 17 wherein magnetite particles having a particle size of from about 50 to about 1500 angstroms are produced.

27. A process of claim 17 wherein the combination is milled for about 1 to 100 hours.

28. A process of claim 17 wherein the combination is milled for about 20 to 40 hours.

29. A process for producing magnetic particles comprising the steps of:
   a. combining a 0.1-40% by weight of an aqueous slurry of a metallocene with a 0.1-40% by weight of an aqueous slurry of a metal hydroxide wherein the metal is selected from the group consisting of iron, cobalt, and nickel; and
   b. milling the combination produced in step (a) for a period of time sufficient to form a slurry of magnetic particles.

* * * * *